(12) United States Patent
Myatt

(10) Patent No.: US 8,168,170 B2
(45) Date of Patent: May 1, 2012

(54) COMPOSITIONS HAVING AN INNER CORE AND AT LEAST THREE SURROUNDING LAYERS

(75) Inventor: Graham John Myatt, Camberley (GB)

(73) Assignees: The Procter and Gamble Company, Cincinnati, OH (US); Alimentary Health Ltd., County Cork (IE)

( * ) Notice: Subject to any disclaimer, the term of this patent is extended or adjusted under 35 U.S.C. 154(b) by 1150 days.

(21) Appl. No.: 10/263,516

(22) Filed: Oct. 3, 2002

(65) Prior Publication Data

US 2004/0120931 A1    Jun. 24, 2004

(51) Int. Cl.
*A01N 63/00*    (2006.01)
(52) U.S. Cl. ........ 424/93.4; 424/439; 424/451; 424/474
(58) Field of Classification Search .................. None
See application file for complete search history.

(56) References Cited

U.S. PATENT DOCUMENTS

| | | | |
|---|---|---|---|
| 2,540,979 A | | 2/1951 | Clymer et al. |
| 3,431,338 A | | 3/1969 | Munzel |
| 3,738,952 A | * | 6/1973 | Signorino ................ 524/77 |
| 4,248,857 A | | 2/1981 | DeNeale et al. |
| 4,816,259 A | | 3/1989 | Matthews et al. |
| 4,927,763 A | * | 5/1990 | Sudoma et al. .......... 435/260 |
| 4,935,247 A | | 6/1990 | Marttila et al. |
| 5,096,717 A | | 3/1992 | Wirth et al. |
| 5,171,580 A | | 12/1992 | Iamartino et al. |
| 5,540,945 A | | 7/1996 | Ikushima |
| 5,629,017 A | | 5/1997 | Pozzi et al. |
| 5,849,327 A | | 12/1998 | Berliner et al. |
| 6,030,641 A | * | 2/2000 | Yamashita et al. ........... 424/451 |
| 6,309,666 B1 | | 10/2001 | Hatano et al. |
| 6,893,662 B2 | | 5/2005 | Dittmar et al. |
| 2001/0018071 A1 | | 8/2001 | Cochran et al. |
| 2002/0098235 A1 | | 7/2002 | Dittmar et al. |
| 2003/0157166 A1 | | 8/2003 | Chen et al. |
| 2003/0190309 A1 | | 10/2003 | Zink et al. |
| 2005/0106133 A1 | | 5/2005 | Zink et al. |

FOREIGN PATENT DOCUMENTS

| | | |
|---|---|---|
| EP | 0212746 A2 | 3/1987 |
| EP | 0212747 A2 | 3/1987 |
| EP | 0439315 B1 | 7/1991 |
| GB | 1190387 | 5/1970 |
| GB | 2245492 A | 8/1992 |
| JP | 62-201823 | 9/1987 |
| JP | 03076561 | 4/1991 |
| JP | 94256170 A | 9/1994 |
| JP | 96242763 A | 9/1996 |
| JP | 2000-191519 | 11/2000 |
| JP | 01278781 A | 10/2001 |
| WO | WO 96/01612 A1 | 1/1996 |
| WO | WO 98/19668 | 5/1998 |
| WO | WO 98/27967 A1 | 7/1998 |
| WO | WO 99/11245 A1 | 3/1999 |
| WO | WO 99/20745 A1 | 4/1999 |
| WO | WO 00/27364 A1 | 5/2000 |
| WO | WO 01/12164 A1 | 2/2001 |
| WO | WO 0112164 A1 | 2/2001 |
| WO | WO 03/045356 A1 | 6/2003 |

OTHER PUBLICATIONS

FreemanLLC.com information on corn zein. Accessed Jul. 20, 2005.3 pages.*
Colorcon, Inc. 2003. "Opaglos." http://www.colorcon.com/pharma/other_prod/opaglos/opaglos_tablet_sealant2.pdf Accessed online Apr. 19, 2006. 2 pages.*
Mills JS et al., eds. 1994. The Organic Chemistry of Museum Objects, 2$^{nd}$ ed. Elsevier Science, Ltd. pp. 115-118.*
Definition of "capsule." Merriam-Webster Online Dictionary, accessed Apr. 19, 2006. 2 pages.*
Lab Prod. Ethiques Ethypharm, "Coated Microgranules Containing a Gastric Protoon Pump Inhibitor With Two Hydrophobic Mateials, Free From Alkali and Any Ionic Surffactant", Derwent Publications Ltd., Ethi May 21, 1999.
Freund Sangyokk, "Capsule Containing Useful Enteric Bacteria— Includes Hydrophobic Layer Non-Fluid at Room Temp Isolating Bacteria From Membrane, to Prevent Moisture Penetration", Derwent Publication Ltd., FREN Aug. 5, 1986.
Morishita Jintan KK, "Capsule Preparation for Enteral Administration of Unsaturated Fatty Acids (Jpn)", Derwent Publications Ltd., MORI Oct. 30, 1997.
Bodmeier R, "Capsule With Controlled Active Ingredient Release Comprises Ingredient-Containing Filling, Capsule Shell, Swelling Agent and Water-Insoluble Layer", BODM/May 18, 1999.
Snow Brand Milk Products, "Enteric Capsules—Comprising Core Containing Drug Etc. and Coating of Hardened Oil of M.Pt. Higher Than Body Temp. and Disintegrated by Lipase in Intestine", SNOW Mar. 31, 1986.
Takeda Chemical Ind KK, "Dry Coated Tablet—Comprises Core Tablets Containing Enzyme Prepn. in Enteric Films Within Outer Shell", TAKE Oct. 5, 1982.
Fujisawa Pharm Co Ltd., "Long-Acting Oral Prepn.—Comprises Rapidly Soluble Innter Layer and Sustained-Release Outer Layer, Both Layers Containing Principal Agent, Which is Coronary or Peripheral Vasodilator (Jpn)", FUJI Sep. 20, 1991.
Eisai KK, "Sustained-Release Solid Prepn. of Zero Order Drug Releasing Profile Comprises Granules Obtainable by Coating Inner Core Containing Xanthine Deriv. Etc. With Film of Hardend Oil", EISA Dec. 22, 1989.
Kyoto Yakuhin KK, "Sustains-Release Formulation Which Floats in Stomach—Comprises Core of Fats and Oils, Coated With Drug Containing Layer of e.g. Agar", KYOT Jul. 10, 1987.
SS Pharmaceutical KK, Tablets Containing Double-Coated Granules—Obtained by Coating With Insol. Polymer, Enteric Polymer and/or Waxes, Then Further Coating With Water or Acid-Soluble Polymer, SSSE Aug. 18, 1988.

(Continued)

*Primary Examiner* — L B Driscoll
(74) *Attorney, Agent, or Firm* — Amanda T. Barry; Kristin Kohler

(57) ABSTRACT

Disclosed are compositions comprising an inner core and at least two surrounding layers. The compositions are suitable for use in humans and other mammals, particularly wherein a component of the inner core is susceptible to moisture. The compositions comprise an inner core comprising one or more components; an inner layer which surrounds the inner core, wherein the inner layer is selected from continuous coatings insoluble at a pH of about 3 or less, continuous coatings having a coating weight of from about 3 mg/cm$^2$, and combinations thereof; and an outer layer which surrounds the inner layer, wherein the outer layer is hydrophobic.

21 Claims, No Drawings

OTHER PUBLICATIONS

Morishita Jintan KK, "Yogurt for Supply Physiologically Important Intestinal Bacteria—Contains Bacteria Contained in Capsule Having Inner Layer Made of Digestible Substance and Outer Layer Dissolving in Intestine", MORI Mar. 10, 1995.

U.S. Appl. No. 12/033,288, filed Feb. 19, 2008.
U.S. Appl. No. 11/981,035, filed Oct. 31, 2007.
U.S. Appl. No. 10/704,253, filed Nov. 7, 2003.

* cited by examiner

COMPOSITIONS HAVING AN INNER CORE AND AT LEAST THREE SURROUNDING LAYERS

FIELD OF THE INVENTION

The present invention relates to compositions that are useful for administration to humans and other mammals. The compositions are particularly useful wherein the composition comprises a component that is susceptible to moisture or may otherwise be compromised by environmental factors. The compositions comprise an inner core and at least two surrounding layers, wherein the surrounding layers protect the inner core from moisture or such other factors.

BACKGROUND OF THE INVENTION

The delivery of biologically active components that are susceptible to moisture or are otherwise compromised by environmental factors has been a continuous problem for those presented with the challenge of formulating such components in a stable product. Indeed, a variety of mechanisms have been proposed, for example, encapsulation of hygroscopic materials or inclusion of agents such as dessicants. However, these mechanisms on their own may not always be suitable or effective for use.

Even further, many components are desirable for delivery to specific locations in the mammalian system, for example, the jejunem, ileum, or other locations in the intestinal tract. Such components are often enterically coated for targeted intestinal delivery and prevention of degradation in acidic environments such as the stomach. However, such enteric coatings may not be effective in preventing moisture from affecting, or coming in contact with, the susceptible component.

For example, it has recently been reported that certain probiotic components that are isolated from healthy gastrointestinal tracts are useful for treating inflammatory conditions such as inflammatory bowel disease or irritable bowel syndrome. Indeed, successful delivery of such components to the inflamed portions of the gastrointestinal tract, for example the intestines, is likely to be an important advance in treating these conditions. However, oral administration of such components has proven challenging, as such probiotic components necessarily pass through non-native locations of the gastrointestinal tract, for example the acidic environment of the stomach, where the probiotic components can be quickly degraded. Moreover, the shelf stability of such components, perhaps primarily due to susceptibility to moisture, may not be suitable or practical for product manufacturers.

As a result, there is a continuing need for compositions that are useful for maintaining the integrity of susceptible probiotics and other components such as vitamins and certain other sensitive biologically active agents. Surprisingly, the present inventors have discovered compositions which are suitable for effective delivery of one or more of such susceptible components. The inventors have discovered that compositions comprising at least two layers surrounding the core which contains the component, wherein the layers are an enteric layer and a hydrophobic layer, respectively, provide surprisingly optimized stability. Such compositions are suitable for use with susceptible components such as probiotics, even wherein an extended shelf life is necessary for commercial delivery. These and other benefits of the present invention are described herein below.

SUMMARY OF THE INVENTION

The present invention relates to compositions containing an inner core and at least two surrounding layers. The compositions are suitable for use in humans and other mammals, particularly wherein a component of the inner core is susceptible to moisture. In particular, the present invention relates to compositions comprising:

(a) an inner core comprising one or more components;

(b) an inner layer which surrounds the inner core, wherein the inner layer is selected from the group consisting of continuous coatings insoluble at a pH of about 3 or less, continuous coatings having a coating weight of from about 3 mg/cm$^2$ to about 25 mg/cm$^2$, and combinations thereof; and (c) an outer layer which surrounds the inner layer, wherein the outer layer is hydrophobic.

In a preferred embodiment of the present invention, the inner core comprises bacteria. Preferred bacteria for use herein include those selected from lactobacillus, bifidobacteria, and mixtures thereof, and other bacteria that are susceptible to moisture or may be otherwise compromised by environmental factors.

DETAILED DESCRIPTION OF THE INVENTION

Various documents including, for example, publications and patents, are recited throughout this disclosure. All such documents are hereby incorporated by reference. The citation of any given document is not to be construed as an admission that it is prior art with respect to the present invention.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the features or embodiments as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

COMPOSITIONS OF THE PRESENT INVENTION

The present invention relates to compositions that are useful for administration to humans and other mammals. The compositions are particularly useful wherein the inner core of the composition comprises a component that is susceptible to moisture or may otherwise be compromised by environmental factors. The compositions comprise the inner core and at least two surrounding layers, wherein the surrounding layers protect the inner core from moisture or such other factors.

The present compositions comprise:
(a) an inner core comprising one or more components;
(b) an inner layer which is contiguous with the inner core, wherein the inner layer is selected from the group consisting of continuous coatings insoluble at a pH of about 3 or less, continuous coatings having a coating weight of from about 3 mg/cm$^2$ to about 25 mg/cm$^2$, and combinations thereof; and
(c) an outer layer which surrounds the inner layer, wherein the outer layer is hydrophobic.

As used herein, the inner layer and outer layer are different compositions relative to each other, i.e., the inner layer does not have the same total chemical composition as the outer layer. Each of the elements of the present invention, including preferred embodiments are described herein as follows:

DEFINITIONS

The layers herein are each joined to the inner core. As used herein, the terms "joined to," "joined to the inner core," or the like means surrounding the inner core in such a manner that the layer is contiguous with either the inner core itself, a preceding layer, or a succeeding layer. The layer may be "joined to" the inner core, a preceding layer, or a succeeding layer even though other matter (such as another preceding or succeeding layer) intervenes. Accordingly, a layer which is "joined to" the inner core need not actually be contiguous with the inner core.

As used herein, the term "contiguous with" means directly joined by physical forces with essentially no intervening matter. For example, the inner layer may be contiguous with the inner core as well as a succeeding layer (wherein the succeeding layer is either another layer or the outer layer). As another example, the outer layer may be contiguous with the inner layer or another layer. The outer layer is not contiguous with the inner core, because the inner layer is a preceding layer relative to the outer layer.

As used herein, the term "preceding layer" means a layer which is joined to the inner core and is closer in proximity to the inner core relative to a reference layer joined to the same inner core. For example, the inner layer is a preceding layer relative to the outer layer.

As used herein, the term "succeeding layer" means a layer which is joined to the inner core but is further in proximity from the inner core relative to a reference layer joined to the same inner core. For example, the outer layer is a succeeding layer relative to the inner layer.

As used herein, coating weights are expressed in terms of mg/cm$^2$, referring to milligrams (mg) of referenced layer per square centimeter (cm$^2$) of referenced layer.

The Inner Core

The inner core comprises one or more components. The components may be any of a variety of materials. A component may be selected from, for example, biologically active components including drug substances, over-the-counter substances, nutriceuticals, dietary supplements, and combinations thereof. Specifically, a component may be selected from, for example, bacteria, vitamins, minerals, fibers, and other biologically active components. A component may also be an excipient, including those that are combined in the composition with a biologically active component.

Preferably, at least one of the components is susceptible to moisture or is otherwise ordinarily compromised by environmental factors. For example, one or more hygroscopic materials may be utilized, as it has been discovered that the present invention is quite suitable for creating a water impermeable barrier. As another preferred embodiment herein, at least one of the components has a water activity of about 0.3 or less, alternatively about 0.2 or less, as measured at a temperature of from about 20° C. to about 25° C. Measurement of water activity is standard in the art. For example, kits are readily available for use in the measurement of water activity, such as a water activity kit commercially available from Csiro, Australia.

In a preferred embodiment of the present invention, at least one component of the inner core is prepared such that the inner core is a low water system. For example, at least one of the components may be freeze-dried, lyophilized, or spray-dried.

The component is also preferably desirable for delivery to the middle and lower gastrointestinal tract, including the duodenum, jejunem, ileum, or colon.

In a preferred embodiment of the present invention, the inner core comprises bacteria. Preferably, the bacteria is a probiotic microorganism. Probiotic microorganisms typically occur in the normal or healthy intestines of humans or other mammals and have been shown to have a beneficial effect on disturbed, diseased, and even healthy gastrointestinal tracts of such mammals. However, probiotic microorganisms may be susceptible to moisture or other environmental factors. The present invention therefore aids the delivery and efficacy of these microorganisms within the present compositions, since the invention may protect against the degradation of the microorganisms either during storage or when administered to a mammal.

Preferably, the probiotic microorganisms are selected from lactobacillus, bifidobacteria, streptococci, and mixtures thereof. Most preferably, the probiotic microorganisms are selected from the group consisting of lactobacillus, bifidobacteria, and mixtures thereof, for example, *Lactobacillus salivarius, Lactobacillus casei, Lactobacillus acidophilus, Lactobacillus plantarum, Lactobacillus rhamnosus, Bifidobacterium bifidum, Bifidobacterium infantis*, and mixtures thereof. Of these examples, *Lactobacillus salivarius, Bifidobacterium infantis*, or mixtures thereof are particularly preferred.

As a non-limiting example, strains of *Bifidobacterium* isolated from resected and washed human gastrointestinal tract as described in Collins et al., WO 00/42168, published Jul. 20, 2000, are particularly preferred. The *Bifidobacterium infantis* strain which is designated as UCC35624 is particularly preferred, described as being deposited at the National Collections of Industrial and Marine Bacteria Limited (MCIMB) on Jan. 13, 1999 and accorded the accession number NCIMB 41003.

As another non-limiting example, strains of *Lactobacillus salivarius* isolated from resected and washed human gastrointestinal tract as described in Collins et al., WO 98/35014, published Aug. 13, 1998, are particularly preferred. The *Lactobacillus salivarius* strains which are designated as UCC 1 and UCC 118 are each particularly preferred, described as being deposited at the National Collections of Industrial and Marine Bacteria Limited (MCIMB) on Nov. 27, 1996 and accorded the accession numbers NCIMB 40830 and 40829, respectively.

In one embodiment of the present invention, the compositions (most preferably, the inner core) comprise at least about $10^6$ cfu, more preferably from about $10^6$ cfu to about $10^{15}$ cfu, even more preferably from about $10^7$ to about $10^{13}$ cfu, and most preferably from about $10^8$ to about $10^{12}$ cfu of bacteria, all per gram of the inner core.

As other examples of inner core components, one or more vitamins may be utilized. Vitamin stability is often influenced by water activity in addition to other environmental factors.

For example, vitamin A, vitamin $B_1$, vitamin $B_2$, vitamin $B_6$, vitamin $B_{12}$, niacin, folic acid, biotin, vitamin C, vitamin D, vitamin E, vitamin K, and mixtures thereof may be used. Fat-soluble vitamins, for example beta-carotene and other source of vitamin A, may be particularly useful for inclusion in the inner core due to their sensitivity to moisture. Vitamin C, vitamin E, and mixtures thereof are also particularly useful.

As yet another example of inner core components, one or more enzymes may be utilized. For example, a proteolytic enzyme (e.g., pancreatin) may be utilized.

Other non-limiting examples of components useful for the inner core include diclofenac, naproxen, aspirin, indomethacin, omeprazole, cardiac glycosides, electrolyte preparations with sodium, potassium, or magnesium salts as well as calcium and iron preparations, bisacodyl preparations, valproic acid, 5-ASA, steroids such as hydrocortisone, budesonide, laxatives, octreotide, cisapride, anticholinergics, calcium channel blockers, 5HT3-antagonists such as ondansetron and peptides such as insulin.

As mentioned, a component of the inner core may be an excipient. Excipients are exceedingly well-known in the art. Non-limiting examples of excipients include sweeteners (such as described herein below); flavor and/or coloring agents (such as described herein below), starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, and polyethylene glycol; alginic acid; emulsifiers, such as TWEENS; wetting agents, such as sodium lauryl sulfate; tabletting agents such as binders, stabilizers; antioxidants; and preservatives.

The inner core may be optionally formed into a tablet or other compressed vehicle. Additionally or alternatively, the inner core may be encapsulated, wherein the composition is a capsule. A capsule layer surrounding the inner core, which is a preferred embodiment of the present invention, is discussed further herein below.

The Optional Capsule Layer

In an optional, but preferred embodiment of the present invention, the compositions comprise a capsule layer that surrounds and is joined to the inner core. Most preferably, this capsule layer is contiguous to the inner core and is a preceding layer relative to the inner layer and outer layer. In this embodiment, the compositions are provided in the form of tablets, capsules, or the like, preferably capsules.

Preferably, the capsule layer comprises a component selected from the group consisting of gelatin (including modified gelatins, for example, gelatin phthalate or gelatin succinate), hydroxypropylmethylcellulose (HPMC), starches, cellulosic polymers, other like polymers, and mixtures thereof. Most preferably, the capsule layer comprises hydroxypropylmethylcellulose (HPMC). In a particularly preferred embodiment of the present compositions, the capsule layer further comprises a plasticizer.

The capsule layers may be filled with the inner core according to standard techniques or may otherwise be joined to the inner core. For example, the capsule layers may be provided, filled with the inner core, sealed if desired, and then further coated with the inner layer and outer layer. To illustrate, hard two-piece capsules may be sealed, for example, via banding or LEMS (liquid encapsulation micro-spray, commercially available from Capsugel (Division of Warner-Lambert Company), Greenwood, S.C., U.S.A.).

The Inner Layer

The inner layer surrounds and is joined to the inner core. The inner layer is selected from continuous coatings which are insoluble at a pH of about 3 or less, continuous coatings having a coating weight of from about 3 mg/cm$^2$ to about 25 mg/cm$^2$, and combinations thereof. As used herein, the term "continuous" means that the layer is not disrupted by a void at any point.

Preferably, the inner layer is a continuous coating which is insoluble at a pH of about 3 or less, alternatively about 4 or less, alternatively about 5 or less. More preferably, such inner layer is soluble at a pH of about 5 or more, alternatively about 5.2 or more, alternatively about 5.5 or more. Most preferably, the inner layer is a continuous coating which is soluble at a pH of from about 5 to about 7, alternatively from about 5.2 to about 6.8, alternatively from about 5.5 to about 6.5. As used herein, the term "insoluble" means that at least about 75% of the referenced layer, by weight of the referenced layer, fails to dissolve in water at a temperature of 25° C. As used herein, the term "soluble" means that at least about 50% of the referenced layer, more preferably at least about 75% of the referenced layer, both by weight of the referenced layer, dissolves in water at a temperature of 25° C.

The thickness of the inner layer may be important for ensuring that the inner layer, and thus the inner core, remains intact until the form reaches the desired site of delivery, for example in the middle or lower intestinal tract. Wherein the inner layer is a continuous coating having a coating weight of from about 3 mg/cm$^2$ to about 25 mg/vm$^2$, the inner coating weight may or may not be insoluble at a pH of about 3 or less. Preferably, however, wherein the inner layer has this coating weight, the inner layer also exhibits an insolubility or solubility as described herein above. Additionally or alternatively, it may be preferable that the inner layer has a coating weight of from about 4 mg/cm$^2$ to about 20 mg/cm$^2$.

Without intending to be limited by theory, it is preferred that the inner layer provides controlled release of the inner core, such that release is accomplished at a location in the middle or lower gastrointestinal tract. The inner layer may prevent or minimize exposure of the susceptible inner core component to the buccal cavity, pharynx, esophagus, and stomach, and to the enzymes and other components associated with these tissues.

The inner layer comprises one or more materials. Non-limiting examples of preferred materials include zein, shellac, cellulosic polymers and copolymers such as hydroxypropyl cellulose, hydroxyethyl cellulose, hydroxypropyl methyl cellulose methyl cellulose, ethyl cellulose, cellulose acetate, cellulose acetate trimellitiate (CAT), hydroxypropylmethyl cellulose phthalate (HPMCP), cellulose acetate phthalate (CAP), hydroxypropylmethyl cellose succinate, and carboxymethylcellulose sodium. Vinyl polymers and copolymers such as polyvinyl acetate phthalate (PVAP), polyvinyl pyrollidone, polyvinyl aceate, vinylacetate crotonic acid copolymer, and ethylene-vinyl acetate copolymers.

Preferably, the inner layer comprises an anionic polymer. The most preferred materials for use in the inner layer include copolymers of methacrylic acid, methacrylate, acrylic acid, or acrylate. Non-limiting examples of such copolymers include those marketed under the term EUDRAGIT, commercially available from Rohm Pharma (Germany). These polymers and copolymers are particularly useful for targeted delivery to the middle or lower gastrointestinal tract. For example, EUDRAGIT L 100-55, EUDRAGIT L 30 D-55 (soluble at pH of about 5.5 or more), EUDRAGIT L 100 (soluble at pH of about 6 or more), and EUDRAGIT S 100 (soluble at pH of about 7 or more), and like polymers.

EUDRAGIT S can be used on its own (i.e., free of other EUDRAGITS or other like materials) for targeted delivery to the colon. Alternatively, EUDRAGIT S, being poorly soluble in intestinal fluids below a pH of about 7, can be used in combination with, for example, EUDRAGIT L-30D (soluble in intestinal fluids having a pH of about 5.5 or greater), in order to provide a delayed relase composition which may deliver an inner core component to various segments of the intestinal tract. For example, wherein more EUDRAGIT L-30D is used, delivery may commence in more proximal segments of the small intestine, but wherein more EUDRAGIT S is used, delivery may commence in more distal segments of the small intestine. In this example, it will be readily appreciated by those ordinarily skilled in the art that both EUDRAGIT L-30D and EUDRAGIT S may be replaced with other polymers or copolymers having similar solubility profiles.

The inner layer is a preceding layer relative to the outer layer (i.e., the outer layer is a succeeding layer relative to the inner layer). The inner layer may optionally be contiguous to the inner core, although one or more other layers may be preceding layers relative to the inner layer. Preferably, the inner layer is contiguous to the (optional) capsule layer, wherein the capsule layer is also contiguous to the inner core (i.e., the inner layer is a succeeding layer relative to the capsule layer).

The inner layer may optionally be contiguous to the outer layer, although one or more other layers may be succeeding layers relative to the inner layer. Preferably, the inner layer is contiguous to the outer layer.

Most preferably, the inner layer is contiguous to a capsule layer (and is a succeeding layer relative to the capsule layer) and is also contiguous to the outer layer (and is a preceding layer relative to the outer layer). In the most preferred embodiment herein, the composition comprises the inner core, a capsule layer, the inner layer, and the outer layer.

The Outer Layer

The outer layer is a continuous hydrophobic coating. As used herein, the term "continuous" means that the layer is not disrupted by a void at any point.

The outer layer therefore comprises one or more materials, such that the outer layer is hydrophobic.

In a preferred, but optional, embodiment of the present invention, the term hydrophobic, with reference to the outer layer, means that the outer layer exhibits a water vapor transmission rate (WVTR) of less than about 200 mg/m$^2$/24 hours as measured using the ISO International Standard entitled "Sheet Materials—Determination of Water Vapour Transmission Rate—Gravimetric (Dish) Method" (Reference Number ISO 2528:1995(E)). In another embodiment, the term hydrophobic, with reference to the outer layer, means that the outer layer has a water vapor transmission rate (WVTR) of less than about 100 mg/m$^2$/24 hours using this Standard.

Non-limiting examples of preferred materials that may be included in the outer layer include fatty acids, fatty acid derivatives, polymers, and mixtures thereof. Most preferably, these materials are hydrophobic, such that the outer layer is made hydrophobic through inclusion of this material. For example, the outer layer may comprise a slip aid (as described later herein).

Fatty acid derivatives can include fats (e.g., fatty acid glyceryl esters, e.g., hydrogenated vegetable oils) and waxes (e.g., animal, fossil, vegetable, mineral, or synthetic waxes, such as carnuba, beeswax, carob, candelilla, ozocerite, polyethylene waxes, paraffin waxes, mixtures thereof, and the like). A wax is particularly preferred. Polymers can include polyvinylpyrrolidone, vinyl acetate, ethyl cellulose, cellulose acetate phthalate (e.g., AQUATERIC), cellulose acetate trimelliate, carboxymethyl ethyl cellulose, hydroxypropyl methyl cellulose acetate succinate, hydroxypropyl methyl cellulose phthalate, mixtures thereof, and the like. Most preferably, the outer layer comprises a material selected from the group consisting of fatty acids, fatty acid derivatives, and mixtures thereof.

In a optional embodiment herein the outer layer is a continuous coating having a coating weight of from about 3 mg/cm$^2$ to about 25 mg/cm$^2$, more preferably from about 4 mg/cm$^2$ to about 20 mg/cm$^2$.

The outer layer is joined to both the inner core and the inner layer. The outer layer is a succeeding layer relative to the inner layer (i.e., the inner layer is a preceding layer relative to the outer layer). The outer layer is not contiguous to the inner core. The outer layer is contiguous to a preceding layer, wherein the preceding layer is preferably the inner layer. Thus, one or more layers may optionally intervene between the outer layer and inner layer. Also optionally, the outer layer may be a preceding layer relative to a layer that is even further in proximity from the inner core. However, most preferably, the outer layer is the outermost layer relative to the inner core.

Optional Components of the Present Compositions

The compositions of the present invention may, independently, comprise additional optional components to enhance their performance. For example, one or more plasticizers, coloring agents, flavoring agents, sweeteners, anti-oxidants, buffering agents, slip aids, other excipients, and the like can be optionally included in the compositions herein. Non-limiting examples of optional components are given below:

Plasticizers

Without intending to be limited by theory, plasticizers cause a composition to become more easily deformed, less brittle, and/or less prone to mechanical damage. Thus, one or more plasticizers may optionally be added to the present compositions, particularly a layer of the composition such that the layer is not susceptible to cracking (creation of voids) which can disrupt the continuous nature of the layer.

Non-limiting examples of plasticizers include phthalates (e.g., diethyl phthalate, dibutyl phthalate, dioctyl phthalate), citrates (e.g., triethyl citrate (e.g., CITROFLEX 2), acetyl triethyl citrate, tributyl citrate, and acetyl tributyl citrate), polyhydric alcohols, (e.g., sorbitol, glycerol), triacetin (glyceryl triacetate), polyethylene glycol (e.g., CARBOWAX 400), polysorbate 80, acetylated monoglycerides, glycerol, propylene glycol, fatty acid esters, surfactant polymers, camphor, silicone oil, castor oil, and mixtures thereof.

The amount of plasticizer used will vary, for example depending on the plasticizer used and the desired character of the final layer (e.g., a soft gelatin layer or a hard gelatin layer). For example, in a preferred embodiment of the present compositions a layer comprising a plasticizer preferably comprises from about 1% to about 60%, more preferably from about 5% to about 40% plasticizer, and most preferably from about 10% to about 35% of the plasticizer, all by weight of the layer comprising the plasticizer.

Coloring Agents

One or more pigments or other suitable coloring agents, such as dyes and lakes, may be incorporated into the compositions. U.S. FD&C dyes (e.g., yellow #5, blue #2, red #40) and/or U.S. FD&C lakes are preferably used. Preferred lakes which may be used in the present invention include, for example, Lake red #40, yellow #6, blue #1, and the like. Additionally, a mixture of U.S. FD&C dyes and/or U.S. FD&C lakes in combination with other conventional food and food colorants may be used. As further examples, Riboflavin and β-carotene may also be used. Additionally, other natural coloring agents may be utilized including, for example, fruit, vegetable, and/or plant extracts such as grape, black currant, aronia, carrot, beetroot, red cabbage, and hibiscus.

The coloring agents used herein may be independently utilized in the inner core, the inner layer, the outer layer, and/or any other layers or components of the present compositions (e.g., the capsule layer, if present). For example, one or more coloring agents may be used in the layer that is least proximal to the inner core in order to impart a desired appearance to the finished composition.

The amount of coloring agent used will vary, depending on the agents used and the character or intensity desired in the finished composition. One of ordinary skill in the art will readily make such determination.

Flavoring Agents

One or more flavoring agents may be incorporated in the compositions of the present invention in order to enhance their palatability, particularly as a component of the layer that is least proximal to the inner core. Any natural or synthetic flavor agent can be used in the present invention. As used herein, such flavors may be synthetic or natural flavors.

For example, one or more botanical and/or fruit flavors may be utilized herein. Particularly preferred fruit flavors are exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, grapefruit flavors, and the like. These fruit flavors can be derived from natural sources such as fruit juices and flavor oils, or may alternatively be synthetically prepared.

The flavoring agents used herein may be independently utilized in the inner core, the inner layer, the outer layer, and/or any other layers or components of the present compositions (e.g., the capsule layer, if present). For example, one or more flavoring agents may be used in the layer that is least proximal to the inner core in order to impart a desired flavor to the finished composition.

The amount of flavoring agent used will vary, depending on the agents used and the character or intensity desired in the finished composition. One of ordinary skill in the art will readily make such determination.

Sweeteners

One or more sweeteners, including for example carbohydrate sweeteners and natural and/or artificial no/low calorie sweeteners may optionally be used herein. For example, the compositions of the present invention can be sweetened with any of the carbohydrate sweeteners, preferably monosaccharides and/or disaccharides. Preferred sugar sweeteners for use in the compositions of the present invention are sucrose, fructose, glucose, maltose, and mixtures thereof.

One or more high intensity sweeteners may be utilized, particularly as a component of the layer that is least proximal to the inner core. For example, one or more of the following sweeteners may be utilized: saccharin, cyclamates, L-aspartyl-L-phenylalanine lower alkyl ester sweeteners (e.g., aspartame); L-aspartyl-D-alanine amides disclosed in U.S. Pat. No. 4,411,925; L-aspartyl-D-serine amides disclosed in U.S. Pat. No. 4,399,163; L-aspartyl-L-1-hydroxymethylalkaneamide sweeteners disclosed in U.S. Pat. No. 4,338,346; L-aspartyl-1-hydroxyethyalkaneamide sweeteners disclosed in U.S. Pat. No. 4,423,029; L-aspartyl-D-phenylglycine ester and amide sweeteners disclosed in European Patent Application 168,112, published Jan. 15, 1986; N—[N-3,3-dimethylbutyl)-L-alpha-aspartyl]-L-phenylalanine 1-methyl ester sweeteners disclosed in WO 99/30576; thaumatin; dihydrochalcones; cyclamates; steviosides; glycyrrhizins, synthetic alkoxy aromatics; sucralose; suosan; miraculin; monellin; sorbitol, xylitol; talin; cyclohexylsulfamates; substituted imidazolines; synthetic sulfamic acids such as acesulfame, acesulfame K and n-substituted sulfamic acids; oximes such as perilartine; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates; erythritol; and mixtures thereof. Aspartame is particularly preferred.

The sweeteners used herein may be independently utilized in the inner core, the inner layer, the outer layer, and/or any other layers or components of the present compositions (e.g., the capsule layer, if present). For example, one or more sweeteners may be used in the layer that is least proximal to the inner core in order to impart a desired sweet character to the finished composition. As a further example, a sweetener may be independently utilized as a component of the inner core, for example, as an excipient.

The amount of sweetener used will vary, depending on the agents used and the character or intensity desired in the finished composition. One of ordinary skill in the art will readily make such determination.

Anti-Oxidants

One or more anti-oxidants may be utilized in the compositions of the present invention. Naturally occurring as well as synthetic anti-oxidants may be used. Non-limiting examples of natural anti-oxidants include tocopherols (e.g., vitamin E), ascorbic acid (e.g., vitamin C), vitamin A (e.g., beta-carotene), grape seed extract, selenium, and coenzyme Q10. Non-limiting examples of synthetic anti-oxidants include butylated hydroxytoluene (BHT), butylated hydroxyanisole (BHA), and propyl gallate. Most preferably, the anti-oxidant is mixed with a component of the inner core.

Buffering Agents

One or more buffering agents may be utilized in the compositions of the present invention in order to, for example, maintain a constant pH within an environment. For example, acetate buffers, citrate buffers, and phosphate buffers may be used. Non-limiting examples include acetic acid, sodium acetate, citric acid, sodium citrate, monobasic sodium phosphate, dibasic sodium phosphate, and sodium chloride. Most preferably, the buffering agent is mixed with a component of the inner core.

Slip Aids

One or more slip aids may optionally be included in the present compositions to improve surface friction, water resistance, abrasion resistance, and/or other mechanical properties of the composition. For example, a slip aid may be included in the layer that is least proximal to the inner core, such that a mammal can more easily swallow the composition when orally administered.

Non-limiting examples of slip aids that may be used include wax additives including, for example, animal, fossil, vegetable, mineral, or synthetic waxes. Preferred wax additives include carnuba, beeswax, carob, candelilla, ozocerite, polyethylene waxes, paraffin waxes, polypropylene waxes, and the like. Other non-limiting examples include surfactants, glycerin, oils, and polyethylene glycols.

The slip aids used herein may be independently utilized in the inner core, the inner layer, the outer layer, and/or any other layers or components of the present compositions (e.g., the capsule layer, if present). For example, one or more slip aids is preferably used in the layer that is least proximal to the inner core. As has been mentioned, the outer layer is preferably this least proximal layer, and a slip aid is often the component utilized therein in order to enhance ease of administration as well as impart the desired hydrophobicity.

The amount of slip aid used will vary, depending on the aid used and the specific purpose of the aid. One of ordinary skill in the art will readily make such determination.

Printed Material

The compositions herein may optionally comprise printed material. For example, the composition may comprise text, words, pictures, symbols, and/or other visible images that may or may not convey useful information to the manufacturer and/or consumer. To illustrate, a capsule may indicate dosage level of a biologically active component, or may indicate a trademark or other like descriptor. Typically, if used, such printed material is printed on the surface of the layer that is least proximate relative to the inner core. Material will be printed on the surface of a composition herein via a variety of well-known methods, for example, passing a capsule over an embossed roller which transfers the material to the capsule.

Methods of Using the Present Compositions

Methods of using the present compositions comprise orally administering (i.e., through ingestion) a composition of the present invention to a mammal, preferably a human, to provide various health benefits. The specific health benefit provided will typically be dependent upon the character of the inner core, as well as that of the inner layer. Frequency of administration is not limited and may be dependent upon the specific character of the composition and the desired health benefits. For example, where the inner core comprises bacteria, certain health benefits may result and be preferred, for example, treatment of inflammation, undesirable gastrointestinal activity, inflammatory bowel disease, irritable bowel syndrome, Crohn's disease, ulcerative colitis, post-infection colitis, and pouchitis. See e.g., WO 00/42168 and WO 00/41707.

As used herein, the term "orally administering" with respect to the mammal (preferably, human) means that the mammal ingests or is directed to ingest one or more compositions of the present invention. Wherein the mammal is directed to ingest one or more of the compositions, such direction may be that which instructs and/or informs the user that use of the composition may and/or will provide one or more general health benefits. For example, such direction may be oral direction (e.g., through oral instruction from, for example, a physician, health professional, sales professional or organization, and/or radio or television media (i.e., advertisement) or written direction (e.g., through written direction from, for example, a physician or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a package containing the composition). As used herein, "written" means through text, words, pictures, symbols, and/or other visible images.

Methods of Making the Present Compositions

The present compositions may be made in accordance with methods which will be well understood in the art, given the guidance of this disclosure. Detailed information relating to materials, equipment, and processes for preparing coated dosage forms may be found in *Pharmaceutical Dosage Forms: Tablets*, Eds. Lieberman et al., (New York, Marcel Dekker, Inc., 1989) and Ansel et al., *Pharmaceutical Dosage Forms and Drug Delivery Systems*, 6$^{th}$ Ed., Media, Pa., Williams & Wilkins, 1995). For example, preparation of the various layers and coating of capsules is well documented, and may often be categorized as follows:
  (a) air suspension coating (e.g., utilizing fluid bed drying);
  (b) pan coating (e.g., utilizing a rotating drum); and
  (c) dip coating (e.g., dipping a capsule into a solution or melt of a material).

The layers described herein may be applied as a solution, wherein a solvent is allowed to volatize, thereby leaving behind a dry coat, or by utilizing a melt wherein the layer is applied warm and allowed to cool.

However, with respect to preparation of the multiple-layered compositions of the present invention, certain considerations should be attended with care. For example, wherein the outer layer is contiguous to the inner layer, the outer layer should be applied without substantial compromise to, or disturbance of, the established inner layer. To illustrate, wherein the inner layer could be solubilized by the solvent used to apply the outer layer, then the outer layer should be applied such that most of this solvent is removed prior to the solution coming into contact with the inner layer. This may be achieved by spraying the outer layer onto the continuous inner layer (which surrounds the inner core and, optionally, the capsule layer). The solvent will substantially evaporate during such spraying. Alternatively or additionally, for example, one may ensure that the inner layer is not mechanically damaged during application of the outer layer. Such damage may occur during air suspension or pan coating, wherein the individual dose forms are tumbled together and/or may contact the walls of the coating device. In these situations, it may be advantageous to include one or more plasticizers as part of the inner layer, to reduce brittleness and enable the layer to become more mechanically robust.

Alternatively or additionally, one may ensure that the inner core will not melt and fluidize at temperatures utilized to apply the various layers of the present compositions. If such melting is a possibility, the coating process(es) should be performed quickly to minimize fluidization of the inner core.

EXAMPLES

The following are non-limiting examples of the present compositions, which are prepared utilizing conventional methods. The following examples are provided to illustrate the invention and are not intended to limit the scope thereof in any manner.

Example 1

A composition in accordance with the present invention is prepared as follows. Five (5) kilograms of hard, banded, two-piece hydroxypropylmethylcellulose (HPMC) capsules (size 3), each containing an inner core comprising about 180 milligrams of freeze-dried probiotic formulation (comprising about $10^{10}$ cfu of *Bifidobacterium infantis*) are obtained. The capsules are tumbled in a pan having an inner diameter of about 25 inches. While maintaining the capsule bed temperature at approximately 25° C., a first coating formulation is sprayed onto the capsules with an in-process evaporation rate of at least about 2.5 grams/minute/kilogram of the capsules, which spraying forms the inner layer. The coating formulation is maintained at a temperature of about 40° C. and comprises EUDRAGIT L30D55 (about 70%, by weight of the first coating formulation), triethyl citrate (about 5%, by weight of the first coating formulation), TWEEN 80 (about 30% aqueous solution, by weight) (about 1%, by weight of the first coating formulation), and about 24% water. Upon achieving a coating weight of about 8 mg/cm$^2$, the capsules coated with the inner layer are subjected to a final drying at about 40° C. for about 5 minutes.

The outer layer is then applied as follows. The coated capsules are tumbled at a temperature of from about 35° C. to about 40° C. in a separate pan having an internal diameter of about 25 inches. Finely powdered carnuba wax (having a particle size of from about 100 microns to about 150 microns) is slowly added to the tumbling capsules until a coating weight of about 10 mg/cm$^2$ is achieved. The composition of this example therefore comprises the inner core, a capsule layer, the inner layer, and the outer layer.

Examples 2-5

A visually appealing capsule is prepared in accordance with Example 1, except that the coating formulation used to prepare the inner layer is modified as follows (with all levels expressed in weight percentage, by weight of the coating formulation):

| Example 2 | Example 3 | Example 4 | Example 5 |
|---|---|---|---|
| EUDRAGIT L30D55 (about 50%) | EUDRAGIT S100 (about 20%) | EUDRAGIT L100 (about 65%) | Hydroxypropylmethyl Cellulose Phthalate (about 50%) |
| Polyethylene Glycol (about 5%) | Polyethylene Glycol (about 7.5%) | Triethyl Citrate (about 5%) | Glycerol (about 5%) |
| Titanium Dioxide (about 1%) | Titanium Dioxide (about 0.5%) | Titanium Dioxide (about 0.25%) | Titanium Dioxide (about 0.25%) |
| Water (about 44%) | FD&C Red #40 (about 0.5%) | FD&C Lake Blue #1 (about 0.25%) | beta-Carotene (about 3%) |
|  | Acetone (about 71.5%) | Talc (about 2.5%) | Potassium Sorbate (about 0.1%) |
|  |  | Water (about 27%) | Sodium Lauryl Sulfate (about 1.5%) |
|  |  |  | Water (about 40.15%) |

The resulting inner layers result in compositions that enhance consumer or patient acceptability and increased dosing compliance, due to the visually appealing coatings.

Examples 6-9

Organoleptically appealing capsules are prepared in accordance with Examples 1, 2, 3, 4 or 5, except that the coating formulation used to prepare the outer layer is modified as follows (with all levels expressed in weight percentage, by weight of the coating formulation used to prepare the outer layer):

| Example 6 | Example 7 | Example 8 | Example 9 |
|---|---|---|---|
| Carnuba Wax (about 95%) | Paraffin Wax (about 92%) | Carnuba Wax (about 88%) | Carnuba Wax (about 90%) |
| ASPARTAME (about 0.5%) | Cyclamate (about 1%) | Ozocerite (about 1%) | Sucralose (about 1%) |
| Orange Flavor, powdered (about 4.5%) | Coolant (about 1%) | Acesulfame K (about 2%) | Talc (about 6%) |
|  | Peppermint Flavor, spray dried (about 6%) | Cocoa Flavor (about 9%) | Peppermint Flavor, spray dried (about 3%) |

The resulting outer layers result in compositions that enhance consumer or patient acceptability and increased dosing compliance, due to the organoleptically appealing coatings.

Example 10

In a modification of the process set forth in Example 1, the outer layer is applied to the capsule using a dip coating process. The capsule comprising the inner core, capsule layer, and inner layer is submerged into melted wax. Once removed, the wax is allowed to solidify. This process is repeated until a continuous coating is produced.

Example 11

In a specific example of the dip coating process used in accordance with Example 10, the inner core comprises acetylsalicylic acid, and is encapsulated by the HPMC capsule layer. The inner layer is prepared, surrounding the capsule layer, and is allowed to dry. This capsule is then dip coated in beeswax at a temperature of about 90° C., then allowed to cool.

What is claimed is:

1. A composition comprising:
    (a) an inner core comprising one or more components, including bacteria, wherein at least one or more components has a water activity of about 0.3 or less as measured at a temperature of from about 20° C. to about 25° C.;
    (b) a capsule layer which is joined to the inner core;
    (c) an inner layer which is joined to the inner core, wherein the inner layer is selected from the group consisting of continuous coatings which are insoluble at a pH of about 3 or less, continuous coatings having a coating weight of from about 3 mg/cm$^2$ to about 25 mg/cm$^2$, and combinations thereof; and wherein the inner layer is an anionic copolymer selected from the group consisting of methacrylic acid, methacrylate, acrylic acid, acrylate and combinations thereof; and
    (d) an outer layer which is joined to the inner core, wherein the outer layer is a continuous hydrophobic coating comprising a material selected from the group consisting of fatty acids, fatty acid derivatives, polymers, and mixtures thereof; and which exhibits a water vapor transmission rate of less than about 200 mg/m$^2$/24 hours; wherein the inner layer is a preceding layer relative to the outer layer.

2. The composition according to claim 1 wherein the inner layer is a continuous coating soluble at a pH of about 5 or more.

3. The composition according to claim 1 wherein the inner layer is soluble at a pH of about 5.5 or more.

4. The composition according to claim 3 wherein the inner layer is contiguous to the capsule layer and the capsule layer is contiguous to the inner core.

5. The composition according to claim 1 wherein at least one of the inner layer and outer layer comprises a plasticizer.

6. The composition according to claim 1 wherein at least one of the inner layer and outer layer has a coating weight of from about 4 mg/cm$^2$ to about 20 mg/cm$^2$.

7. The composition according to claim 1 wherein the outer layer comprises a component selected from the group consisting of coloring agents, flavoring agents, sweeteners, antioxidants, buffering agents, surfactants, talc, and mixtures thereof.

8. The composition according to claim 1 wherein the bacteria is a probiotic microorganism.

9. The composition according to claim 8 wherein the inner layer is soluble at a pH of about 5 or more.

10. The composition according to claim 8 wherein the inner layer is soluble at a pH of about 5.5 or more.

11. The composition according to claim 10 wherein the inner layer is contiguous to the capsule layer and the capsule layer is contiguous to the inner core.

12. The composition according to claim 8 wherein at least one of the inner layer and outer layer comprises a plasticizer.

13. The composition according to claim 12 wherein at least one of the inner layer and outer layer has a coating weight of from about 4 $mg/cm^2$ to about 20 $mg/cm^2$.

14. The composition according to claim 12 wherein the outer layer comprises a component selected from the group consisting of coloring agents, flavoring agents, sweeteners, anti-oxidants, buffering agents, surfactants, talc, and mixtures thereof.

15. The composition according to claim 1 wherein at least a plurality of the bacteria is selected from the group consisting of lactobacillus, bifidobacteria, and mixtures thereof.

16. The composition according to claim 15 wherein the inner layer is soluble at a pH of about 5 or more.

17. The composition according to claim 15 wherein the inner layer is soluble at a pH of about 5.5 or more.

18. The composition according to claim 17 wherein the inner layer is contiguous to the capsule layer and the capsule layer is contiguous to the inner core.

19. The composition according to claim 15 wherein at least one of the inner layer and outer layer comprises a plasticizer.

20. The composition according to claim 15 wherein at least one of the inner layer and outer layer has a coating weight of from about 4 $mg/cm^2$ to about 20 $mg/cm^2$.

21. The composition according to claim 15 wherein the outer layer comprises a component selected from the group consisting of coloring agents, flavoring agents, sweeteners, antioxidants, buffering agents, surfactants, talc, and mixtures thereof.

* * * * *